United States Patent
Croke et al.

(10) Patent No.: US 6,176,248 B1
(45) Date of Patent: Jan. 23, 2001

(54) SUBMERGED HYDRAULIC VALUE ACTUATOR WITH LEAK PROTECTION

(75) Inventors: William M. Croke, Slidell; Robert A. Levine, Harvey, both of LA (US)

(73) Assignee: Phillips Petroleum Company, Bartlesville, OK (US)

(*) Notice: Under 35 U.S.C. 154(b), the term of this patent shall be extended for 0 days.

(21) Appl. No.: 09/145,188

(22) Filed: Sep. 1, 1998

(51) Int. Cl.[7] .............. B08B 3/04; B08B 9/032; F16L 9/18

(52) U.S. Cl. .................... 137/15.05; 73/863.72; 73/864.63; 73/864.67; 138/104; 138/114; 137/1; 137/15.04; 137/312; 114/198

(58) Field of Search .................. 137/312, 315, 137/15, 15.04, 15.05, 238, 240, 315.01, 315.11; 138/104, 113, 114; 285/13, 123.1; 73/863.72, 863.73, 864.31, 864.63, 864.67; 114/198, 244, 245

(56) References Cited

U.S. PATENT DOCUMENTS

| | | | |
|---|---|---|---|
| 2,200,310 | 5/1940 | Thayer et al. | 340/605 |
| 2,430,122 | 11/1947 | Grace | 137/551 |
| 2,838,074 * | 6/1958 | Lauck | 138/114 |
| 3,098,246 * | 7/1963 | Pekor et al. | 138/114 |
| 3,299,417 * | 1/1967 | Sibthorpe | 138/114 |
| 3,379,027 * | 4/1968 | Mowell et al. | 138/113 |
| 3,523,579 | 8/1970 | Nelson | 166/337 |
| 3,712,330 * | 1/1973 | Davis | 137/312 |
| 3,841,156 * | 10/1974 | Wolfe | 73/864.31 |
| 4,037,477 * | 7/1977 | Niskin | 73/864.67 |
| 4,089,209 * | 5/1978 | Grana et al. | 73/864.63 |
| 4,091,676 * | 5/1978 | Niskin | 73/864.67 |
| 4,341,235 * | 7/1982 | Nord | 137/312 |
| 4,387,735 * | 6/1983 | Ripert | 137/315.11 |
| 4,426,888 * | 1/1984 | Smith | 73/863.83 |
| 4,431,022 * | 2/1984 | Ripert | 137/315.11 |
| 4,437,486 * | 3/1984 | Bianchi | 137/315.11 |
| 4,462,265 * | 7/1984 | Rein | 73/863.33 |
| 4,471,799 * | 9/1984 | Buck | 137/315.11 |
| 4,644,780 * | 2/1987 | Jeter | 138/114 |
| 4,722,662 | 2/1988 | Morgan | 415/168 |
| 4,852,413 * | 8/1989 | Niskin et al. | 73/864.67 |
| 5,341,857 * | 8/1994 | Bravo | 137/312 |
| 5,356,112 | 10/1994 | Simar et al. | 251/129.11 |
| 5,383,351 | 1/1995 | Kotlyar | 73/46 |
| 5,429,151 * | 7/1995 | Millett et al. | 251/152 |
| 5,884,657 * | 3/1999 | Srock | 138/114 |

* cited by examiner

*Primary Examiner*—George L. Walton
(74) *Attorney, Agent, or Firm*—Drude Faulconer

(57) ABSTRACT

A submerged, valve assembly for controlling flow of fluid (e.g. ballast water) to and from a reservoir (e.g. a ballast tank of a ship. The valve assembly is comprised of a valve which is controlled by a hydraulic valve actuator. A fluid-tight housing encloses the actuator so that any leaking hydraulic fluid will be contained within the housing and will not pollute the surrounding fluid in the tank. The assembly includes a means for detecting any hydraulic fluid which may leak into the housing.

7 Claims, 2 Drawing Sheets

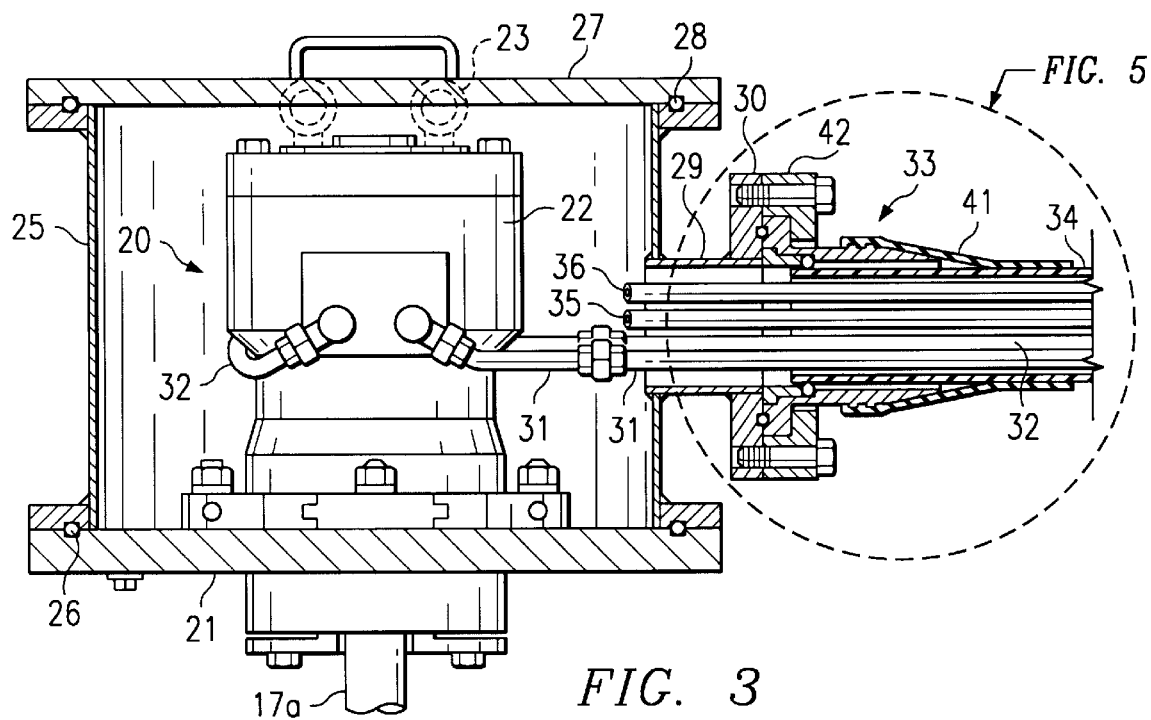
FIG. 3
FIG. 5
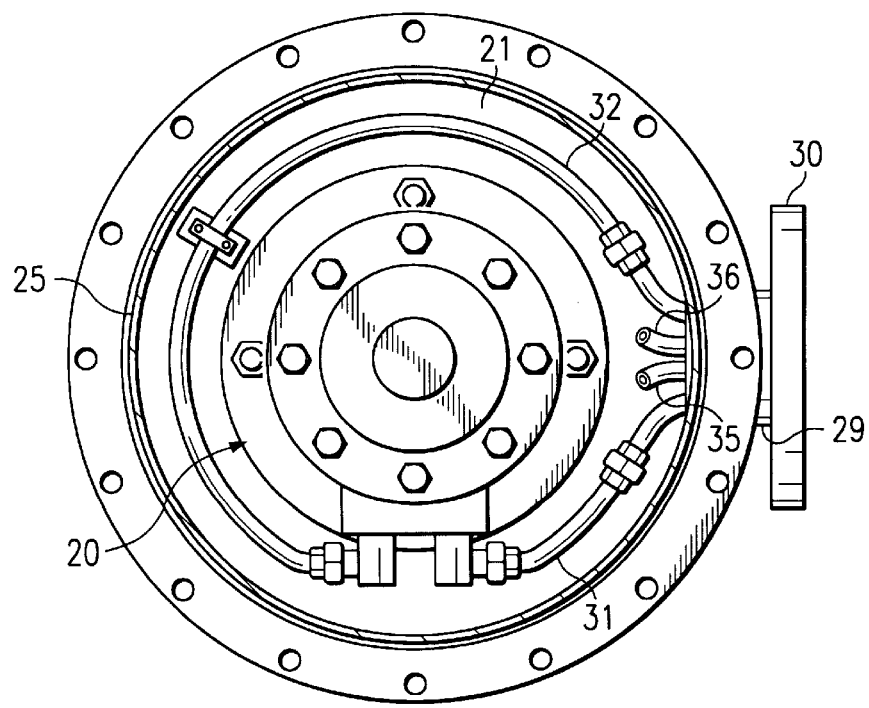
FIG. 4

SUBMERGED HYDRAULIC VALUE ACTUATOR WITH LEAK PROTECTION

DESCRIPTION

1. Technical Field

The present invention relates to a submerged, hydraulic valve actuator with leak protection and a method for detecting such leaks and in one aspect relates to a hydraulic valve actuator of the type used in a submerged location within a ballast water tank aboard a tanker or the like wherein said actuator is encased in a housing so that any hydraulic-fluid leaks are contained therein and wherein such leaks can readily be detected.

2. Background

Double hull tankers are now widely-used for transporting petroleum and petroleum products by sea. It is not uncommon in tankers of this type to use the space between the inner hull and the outer hull as ballast space (i.e. tanks for containing seawater). However, using this space as ballast tanks presents problems when it comes to operating and maintaining the valves which control the flow of seawater into and out of the tanks. Normally, these valves and their respective actuators must be submerged within the tanks, themselves, near the inlet/outlet of the respective tanks and are thereby constantly exposed to the corrosive effects of seawater.

Due to their location, the use of electrically-powered actuators is neither safe nor practical. Further, the location of the valves and the force required to operate such valves also makes the use of purely, mechanical actuators impractical. Instead, submerged, hydraulically-controlled actuators are now in wide use for operating these ballast-water valves. However, the placement of the necessary hydraulic components within the ballast tanks presents a high level of risk for the valve actuators and fittings since they are subject to corrosion which, if left unchecked, can cause the components to fail thus compromising the integrity of the hydraulic system.

For example, if the fittings or the hoses which service the submerged actuators corrode and spring a leak, the hydraulic fluid will leak into the seawater within the ballast tank and will be expelled therewith into the sea when the ballast water is dumped from the tank. As will be recognized, this can pollute the environment and accordingly is unacceptable. Further, due to the submerged position of the actuators within the ballast tank, routine inspection of the actuators is difficult and early detection of failure in the hydraulic system is not likely. Therefore, it is desirable to be able to detect leakage of hydraulic fluid from these actuators at an early stage so that corrective measures may be taken and excessive pollution can be prevented.

SUMMARY OF THE INVENTION

The present invention provides a valve assembly which is adapted to be submerged in a liquid such as the ballast water in a ballast tank of a ship such as a tanker. The valve assembly is comprised of a valve which is movable between an open and a closed position to control the flow of the ballast water therethrough. A hydraulic valve actuator is connected to the valve to move the valve between its open and closed positions. In accordance with the present invention, a fluid-tight housing encloses the hydraulic actuator so that any hydraulic fluid which may leak from the hydraulic actuator or its control lines within said housing will be contained within the housing and will not pollute the surrounding ballast water in the tank. The assembly includes a means for detecting any hydraulic fluid which may leak into the housing.

More specifically, the valve assembly of the present invention is comprised of a valve for controlling the flow of ballast water into and out of a ballast tank of a ship. The valve assembly is submerged in the ballast water and is comprised of a valve which, in turn, is opened and closed by a hydraulic actuator. A housing is positioned over the actuator and is sealed to contain any hydraulic fluid which may leak from the actuator or its control lines within the housing.

The control lines for the actuator are comprised of a first pair of tubes which extend from outside the ballast tank and pass to the actuator through an inlet conduit on an opening in the housing. One of the first pair of tubes supplies the hydraulic fluid to the actuator while the other of the first pair of tubes serves as an exhaust, return line for the power fluid. A second pair of tubes extend from outside of the ballast tank and through the inlet conduit into the inside of the housing. One of the second pair of tubes provides a passage for a purge fluid (e.g. air) into the housing while the other of the second pair of tubes provides a return passage for the purged vapors from the housing. By analyzing the return vapors, it can be determined whether or not any hydraulic fluid has leaked into the housing and the proper corrective measures can be taken.

Both pairs of tubes are encased as a bundle within a single conduit which, in turn, has a flange thereon which mates with a flange on the inlet conduit of the housing. This bundle of tubes within the conduit makes for easy handling while the conduit also protects the ballast water against leakage from the tubes passing therethrough.

BRIEF DESCRIPTION OF THE DRAWINGS

The actual construction, operation, and apparent advantages of the present invention will be better understood by referring to the drawings which are not necessarily to scale and in which like numerals identify like parts and in which:

FIG. 3 is an enlarged, perspective view, partly in section of the hydraulic valve actuator of FIG. 2 within the fluid-tight housing of the present invention;

FIG. 4 is the top view of FIG. 3; and

BEST KNOWN MODE FOR CARRYING OUT THE INVENTION

Figure 1:
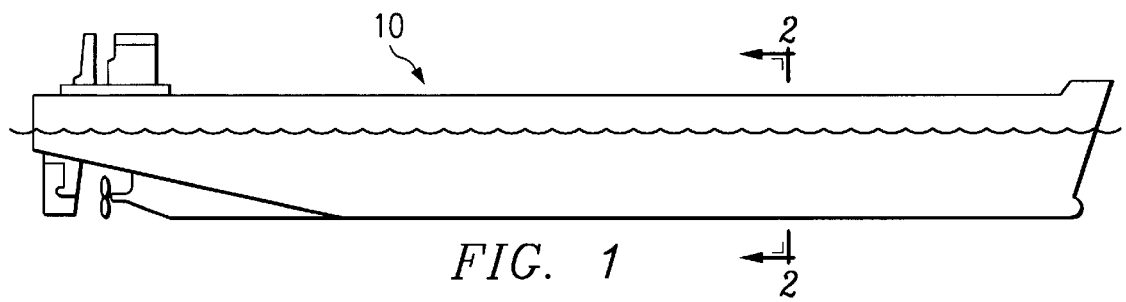
FIG. 1 is a perspective view of a typical sea-going tanker aboard which the present invention may find application.
Figure 2:
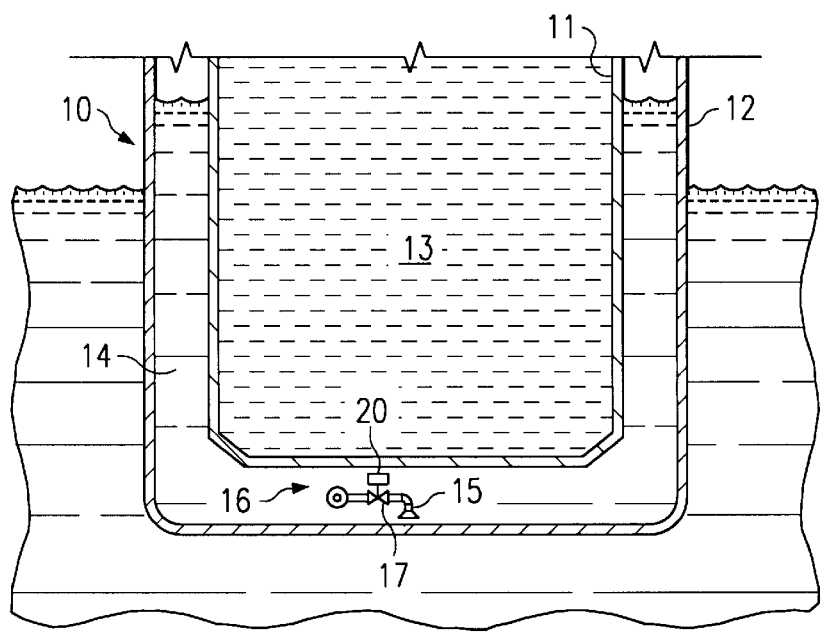
FIG. 2 is a sectional view taken along line 2—2 in FIG. 1

Referring more particularly to the drawings, FIGS. 1 and 2 illustrate a typical double-hull tanker 10 of the type used to transport petroleum and/or petroleum products wherein the body of the tanker is comprised of an inner hull 11 and an outer hull 12 (see FIG. 2). The cargo tank(s) 13 are normally formed within inner hull 11 while the space 14 between the hulls forms ballast tanks for the tanker. As will be understood in the art, ballast (e.g. seawater) is either pumped into or out of tank(s) 14 to maintain the proper draft and stability for the tanker as cargo is loaded/unloaded into or from tank(s) 13. The ballast water is pumped into/from tank(s) 14 through discharge/suction pipe 15 which, in turn, is controlled by valve assembly 16.

Valve assembly 16 is comprised of valve 17 which has an open and a closed position for controlling flow therethrough. Valve 17 may be of any type of appropriate valve (e.g. ball valve, etc.) having a shaft 17a (FIG. 3) which, in turn, is moved between its open and closed positions (e.g. rotated) by hydraulic valve actuator 20. As will be understood in the art, this type of actuator has a spline adapter (not shown) which receives shaft 17a of valve 16 to provide a driving connection between the actuator and the valve. This type of actuator is known and is commercially-available; e.g. Hydraulic Double-Acting Balanced Rotary Actuator, Model BRC 002M-BRC 092, distributed by Danfoss Fluid Power, Racine, Wis.

As best seen in FIGS. 3 and 4, actuator 20 is positioned and is bolted or otherwise secured onto plate 21 of valve assembly 16 which in turn, is fully submerged in ballast tank 14. Actuator 20 has a body 22 which encloses the gearing and associated hydraulic motor (details not shown) necessary for driving shaft 17a of valve 16. Lifting eyes 23 may be attached to the body 22 to aid in positioning the actuator 20 during the installation or replacement as is typical with this type of actuator.

In accordance with the present invention, valve actuator 20 is coupled to valve shaft 17a and is secured onto plate 21. Valve actuator 20 is then enclosed within a fluid-tight housing 25 which is bolted or otherwise secured to plate 21 around actuator 20. An O-ring 26 or other appropriate sealing means is positioned between housing 25 and plate 21 to prevent fluid flow therebetween. The top of housing 25 is closed by cover plate 27 and is made fluid-tight by means of O-ring 28 or the like between housing 25 and cover plate 27. Housing 25 has an inlet conduit 29 extending from an opening therein therein and has a flange 30 thereon for a purpose explained later.

Hydraulic fluid is supplied to actuator 20 through a first pair of tubes 31, 32 which are connected to actuator 20 and which extend from housing 25 through inlet conduit 29 to a source (not shown) outside tank 14. The first pair of tubes 31, 32, form part of tubing bundle 33 which, in turn, is comprised of an outer casing 34 (e.g. conduit of PVC or the like). A second pair of tubes 35, 36 also extend through casing 34 from outside of ballast tank 14, through inlet conduit 29, and both terminate within housing 25 for a purpose discussed below.

Figure 5:
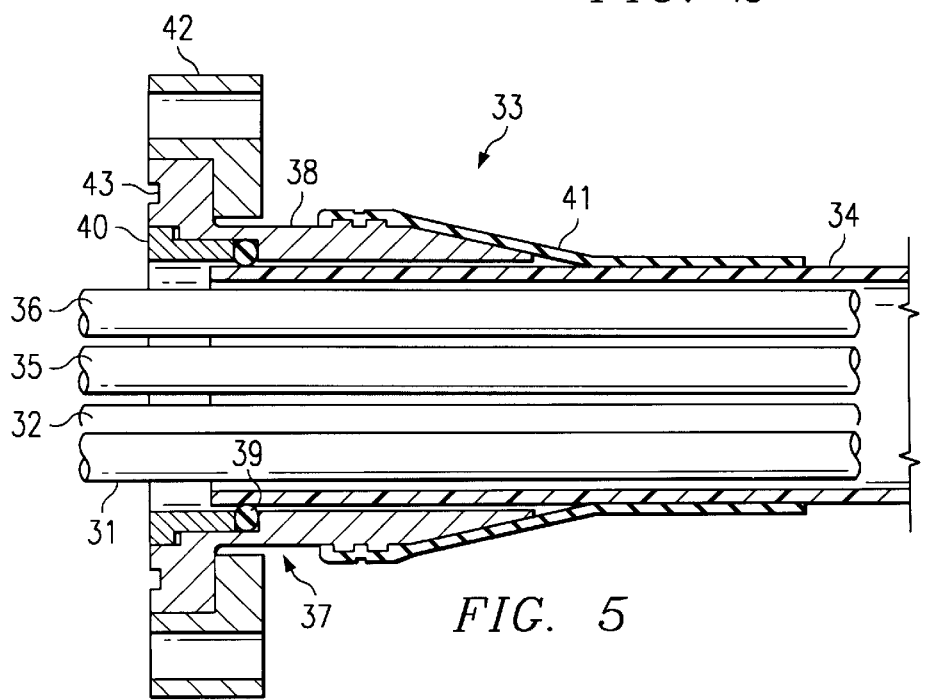
FIG. 5 is an enlarged view, partly in section, taken within line 5—5 of FIG. 3.

Casing 34 has a fluid-tight connector 37 on its outer end which is comprised of a sleeve 38 which slips over casing 34 and has an O-ring 39 therebetween and which is held in place by spacer ring 40. Sleeve 38 is further sealed onto casing 34 by means of a sleeve of commercially-available shrink tubing 41 or the like. Once connector 37 is assembled, it is connected to housing 25 by bolting flange 42 to flange 30. Appropriate O-ring(s) or other seals (not shown) are positioned between the flanges (i.e. in groove 43 in sleeve 41, FIG. 5) to provide a fluid-tight seal therebetween.

Tubing bundle 33 provides a watertight connection between the casing 34, which carries all of the tubes, and the housing 25 and can readily be installed and disconnected without compromising the seal between the tubing bundle 33 and the sleeve 38. This can be of extreme importance when replacing or servicing the valve actuator 20.

In operation, the valve assembly 16 is installed within ballast tank 14. In this position, it will normally be submerged in seawater and will be subject to the corrosive effects thereof. Hydraulic fluid is supplied to actuator 20 through the first pair of tubes 31, 32 to open/close valve 17 to flood/empty tank 14 with seawater as the situation dictates. If for any reason, there is any leakage of hydraulic fluid at the actuator, the fluid will collect within the fluid-tight chamber within housing 25 and will not flow into the seawater within tank 14. It can be seen that by containing the hydraulic fluid within housing 25, no hydraulic fluid will be present in the seawater within tank 14 and therefor none will pollute the sea when the seawater is emptied from tank 14.

In order to monitor the condition of the hydraulic actuator 20 and the supply lines (i.e. first pair of tubes 31, 32), a sample of the environment within housing 25 can be taken at any time by purging housing 25 through the purge lines (i.e. second pair of tubes 35, 36). If there is sufficient pressure within housing 25, this sample may be taken by merely opening one of the purge lines and allowing the sample to flow therethrough. However, if the pressures are not sufficient, then a purge fluid (e.g. air or inert gas) can be flowed under pressure through one of the purge lines with returns being taken through the other purge line. The return purge line can be connected to any appropriated gas detector or analyzer (not shown) whereby the return vapors can be analyzed to determine whether or not there has been a leak within the housing. Detection of hydrocarbon vapors will indicate a leak into housing 25. This will identify and isolate the area of any problems as they arise and will allow the defective equipment to be repaired or replaced at the earliest opportunity.

What is claimed is:

1. A valve assembly adapted to be submerged in a liquid, said assembly comprising:
    a valve having an open and a closed position for controlling the flow of said liquid therethrough;
    a hydraulic actuator connected to said valve for moving said valve between said open and closed positions;
    a fluid tight housing enclosing said hydraulic actuator wherein any hydraulic fluid which may leak from said hydraulic actuator is contained within said housing; and
    means for detecting hydraulic fluid which may leak into said housing, said means comprising:
        at least one line in fluid communication with the interior of said housing and adapted to extend to a point outside of said liquid in which said valve assembly is submerged whereby a sample of the environment within said housing can be withdrawn through said at least one line for analysis to determine if hydraulic fluid is present in said sample.

2. The valve assembly of claim 1 wherein said a least one line for detecting hydraulic fluid comprises:
    a pair of lines in fluid communication with the interior of said housing and adapted to extend to a point outside said liquid in which the valve assembly is submerged, one of said pair of lines being adapted to provide a passage for a purge fluid under pressure into said housing while the other of said pair of lines being adapted to provide a return passage for said purge fluid and a sample of the environment from within said housing to said outside point for analysis to determine if hydraulic fluid is present in said sample.

3. The valve assembly of claim 2 wherein said liquid in which said valve assembly is submerged in water within a ballast tank of a ship.

4. A valve assembly for controlling the flow of ballast water into/out of the ballast tank of a tanker vessel, said valve assembly being submerged within said ballast water and comprising:
    a valve having an open position and a closed position for controlling the flow of ballast water into/out of said ballast tank;

a hydraulic actuator connected to said valve and adapted to move said valve between said open and closed positions;

a fluid tight housing positioned over said hydraulic actuator and having an opening therein;

a first pair of tubes passing through said opening in said housing and fluidly connected to said valve actuator, one of said first pair of tubes being adapted to supply hydraulic fluid to said actuator while the other of said first pair of tubes being adapted to exhaust the hydraulic fluid from said actuator; and means for detecting any hydraulic fluid which may leak into said housing from said first pair of tubes or from said actuator, said means comprising:

a second pair of tubes extending through said opening in said housing, one of said second pair of tubes being adapted to provide a passage for a purge fluid under pressure while the other of said second pair of tubes being adapted to a return passage for said purge fluid and a sample of the environment from within said housing to said outside point for analysis to determine if hydraulic fluid is present in said sample.

5. The valve assembly of claim 4 including:

a inlet conduit connected to said opening in said housing and having a flange thereon;

a casing surrounding both said first and said second pairs of tubes, said casing having a flange; and means for sealing said flange on said casing to said flange on said inlet conduit.

6. A method for detecting a leak of hydraulic fluid around a hydraulic valve actuator which is submerged in a ballast water tank, said method comprising:

positioning a housing around said valve actuator to isolate said actuator from said ballast water; and purging the inside of said housing to recover vapors from within said housing; and analyzing said recovered vapors to determine if any hydraulic fluid has leaked into said housing.

7. The method of claim 6 wherein said purging of said housing comprises:

forcing a fluid into said housing through a first tube which extends from outside said ballast tank into said housing; and recovering said fluid and at least some of any hydraulic fluid through a second, return tube which extends from inside said housing to outside said ballast tank.

* * * * *